United States Patent
Kim et al.

(10) Patent No.: US 9,420,982 B2
(45) Date of Patent: Aug. 23, 2016

(54) MAMMOGRAPHY DETECTOR HAVING MULTIPLE SENSORS, AND MAMMOGRAPHY DEVICE CAPABLE OF ACQUIRING 3D IMAGE ACQUISITION

(75) Inventors: Tae Woo Kim, Gyeonggi-do (KR); Chang Hyeuk Kim, Seoul (KR)

(73) Assignees: Rayence Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 288 days.

(21) Appl. No.: 14/130,574

(22) PCT Filed: Jul. 1, 2011

(86) PCT No.: PCT/KR2011/004868
§ 371 (c)(1),
(2), (4) Date: Mar. 20, 2014

(87) PCT Pub. No.: WO2013/005871
PCT Pub. Date: Jan. 10, 2013

(65) Prior Publication Data
US 2014/0205060 A1    Jul. 24, 2014

(51) Int. Cl.
*A61B 6/00* (2006.01)
*A61B 6/03* (2006.01)
(Continued)

(52) U.S. Cl.
CPC .................. *A61B 6/502* (2013.01); *A61B 6/032* (2013.01); *A61B 6/4233* (2013.01); *A61B 6/4266* (2013.01); *A61B 6/4441* (2013.01); *A61B 6/0414* (2013.01); *A61B 6/107* (2013.01); *A61B 6/4283* (2013.01); *A61B 6/4411* (2013.01); *A61B 6/4476* (2013.01); *A61B 6/5235* (2013.01)

(58) Field of Classification Search
CPC ...... A61B 6/025; A61B 6/032; A61B 6/0414; A61B 6/4208; A61B 6/4233; A61B 6/4266; A61B 6/4283; A61B 6/502
USPC .......... 378/22, 25, 26, 37, 98.8, 196–198, 19; 250/370.09
See application file for complete search history.

(56) References Cited

U.S. PATENT DOCUMENTS

| 6,442,238 B2 * | 8/2002 | Meulenbrugge | G01T 1/2002 250/366 |
| 6,999,554 B2 * | 2/2006 | Mertelmeier | A61B 6/502 378/196 |
| 7,092,483 B2 * | 8/2006 | Nyholm | A61B 6/06 378/38 |

(Continued)

FOREIGN PATENT DOCUMENTS

| JP | 2007-289640 A | 11/2007 |
| JP | 2008-104673 A | 5/2008 |

(Continued)

*Primary Examiner* — Allen C. Ho
(74) *Attorney, Agent, or Firm* — IP Legal Services, LLC (57) ABSTRACT

The disclosure relates to a mammography device including a main body, a gantry, an X-ray generator, an X-ray detector, a first rotating shaft, a supporting panel, and a pressing panel. The gantry is vertically movably connected to the main body. The X-ray generator is attached to one end of the gantry. The X-ray detector is attached to the other end of the gantry. The first rotating shaft is configured to rotate the gantry. The support panel is configured to support a patient's breast. The pressing panel is vertically movably disposed and connected to the main body. Such a pressing panel is configured to press the patient's breast on the support panel. The X-ray detector acquires 3-D images while rotating the gantry around the breast pressed by the pressing panel and the support panel.

13 Claims, 5 Drawing Sheets

(51) Int. Cl.
*A61B 6/04* (2006.01)
*A61B 6/10* (2006.01)

(56) References Cited

U.S. PATENT DOCUMENTS

| | | | | |
|---|---|---|---|---|
| 7,123,684 B2* | 10/2006 | Jing | ...................... | A61B 6/502 |
| | | | | 378/22 |
| 7,245,694 B2* | 7/2007 | Jing | ...................... | A61B 6/025 |
| | | | | 378/37 |
| 7,453,979 B2 | 11/2008 | Sendai | | |
| 7,463,713 B2* | 12/2008 | Mertelmeier | .......... | A61B 6/025 |
| | | | | 378/22 |
| 7,545,907 B2* | 6/2009 | Stewart | ................... | A61B 6/02 |
| | | | | 378/22 |
| 7,558,366 B2* | 7/2009 | Barth | .................... | G06T 11/006 |
| | | | | 378/197 |
| 7,613,276 B2 | 11/2009 | Sendai | | |
| 7,693,254 B2* | 4/2010 | Muller | ................. | G06T 11/008 |
| | | | | 378/37 |
| 7,697,661 B2* | 4/2010 | Souchay | ................ | A61B 6/025 |
| | | | | 378/21 |
| 7,798,708 B2* | 9/2010 | Erhardt | ................. | A61B 6/032 |
| | | | | 250/370.09 |
| 7,817,773 B2* | 10/2010 | Stanton | ................. | A61B 6/466 |
| | | | | 378/15 |
| 7,831,296 B2* | 11/2010 | DeFreitas | .............. | A61B 6/502 |
| | | | | 378/37 |
| 7,835,490 B2* | 11/2010 | Ramsauer | ........... | A61B 6/0414 |
| | | | | 378/197 |
| 7,835,491 B2* | 11/2010 | Fischer | ................. | A61B 6/502 |
| | | | | 378/37 |
| 7,853,064 B2* | 12/2010 | Bernard | .............. | G06T 7/0012 |
| | | | | 378/37 |
| 7,869,563 B2* | 1/2011 | Defreitas | ............... | A61B 6/502 |
| | | | | 378/114 |
| 7,881,513 B2* | 2/2011 | Bernard | ................ | G06T 7/0012 |
| | | | | 378/21 |
| 7,885,378 B2* | 2/2011 | Kopans | .................. | A61B 6/025 |
| | | | | 378/13 |
| 7,965,812 B2* | 6/2011 | Hanke | .................... | A61B 6/502 |
| | | | | 378/21 |
| 8,031,834 B2* | 10/2011 | Ludwig | .................. | A61B 6/025 |
| | | | | 378/22 |
| 8,152,373 B2* | 4/2012 | Erhardt | .................. | A61B 6/032 |
| | | | | 250/370.09 |
| 8,184,770 B2* | 5/2012 | Fischer | .................. | A61B 6/022 |
| | | | | 378/37 |
| 8,194,819 B2* | 6/2012 | Eliasson | ................ | A61B 6/025 |
| | | | | 378/189 |
| 8,363,050 B2* | 1/2013 | Ludwig | .................. | A61B 6/025 |
| | | | | 345/419 |
| 8,411,923 B2* | 4/2013 | Ludwig | .................. | A61B 6/02 |
| | | | | 378/4 |
| 8,553,837 B2* | 10/2013 | Johansson | .............. | A61B 6/205 |
| | | | | 378/22 |
| 8,565,372 B2* | 10/2013 | Stein | ...................... | A61B 6/025 |
| | | | | 378/116 |
| 8,576,988 B2* | 11/2013 | Lewalter | ............ | A61B 6/4028 |
| | | | | 378/126 |
| 8,787,522 B2* | 7/2014 | Smith | .................... | A61B 6/025 |
| | | | | 378/20 |
| 8,792,617 B2* | 7/2014 | Baetz | ................... | A61B 6/4035 |
| | | | | 378/16 |
| 9,176,372 B2* | 11/2015 | Erhardt | .................. | A61B 6/032 |
| | | | | 250/370.09 |

FOREIGN PATENT DOCUMENTS

| | | |
|---|---|---|
| JP | 2010-069241 A | 4/2010 |
| KR | 10-2010-0012616 A | 2/2010 |
| KR | 10-2010-0043334 A | 4/2010 |
| KR | 10-2013-0003271 A | 1/2013 |
| WO | 2010/028208 A1 | 3/2010 |

\* cited by examiner

MAMMOGRAPHY DETECTOR HAVING MULTIPLE SENSORS, AND MAMMOGRAPHY DEVICE CAPABLE OF ACQUIRING 3D IMAGE ACQUISITION

CROSS REFERENCE TO RELATED APPLICATIONS

This application is a National Stage Patent Application of PCT International Patent Application No. PCT/KR2011/004868 (filed on Jul. 1, 2011) under 35 U.S.C. §371, the teaching of which is incorporated herein in its entirety by reference.

TECHNICAL FIELD

The present invention relates to a mammography detector having multiple sensors and a mammography device capable of acquiring a 3D image, and more particularly, to a mammography detector provided with multiple sensors such as a high-definition sensor for detecting a very small lesion, a high-contrast sensor for detecting an accurate size of a lesion, and a mammography sensor, or a CT sensor for mammography and a mammography device which can rotate an X-ray generator and the mammography detector by 185 degrees or more relative to a measurement target breast and which can acquire a 3D image.

BACKGROUND ART

In general, a mammography device is a radiography device used to diagnose a breast cancer in an early stage, and acquires a two-dimensional image for diagnosing abreast cancer by causing X-rays to pass through a breast of an examinee with a predetermined dose and detecting the dose of transmitted X-rays using an X-ray sensitive film.

In recent years, a mammography device employs a method of digitally acquiring a two-dimensional image using an image sensor instead of the X-ray sensitive film. Such a mammography device has a structure in which a breast pressing member is interposed between an X-ray generator and a digital X-ray detector so as to cause the breast pressing member to press a breast for radiography in a state where the breast is placed on the digital X-ray detector.

Figure 1:
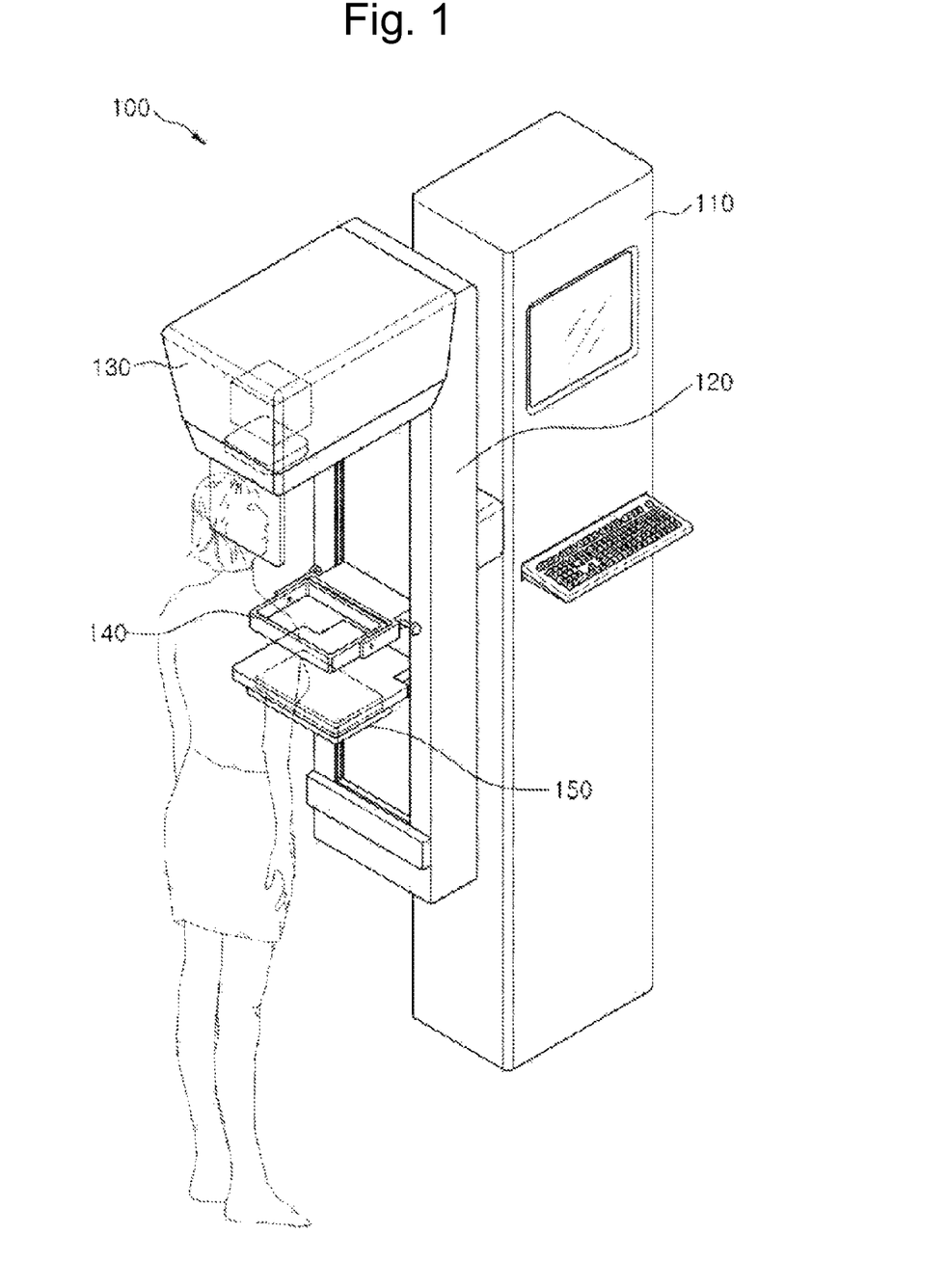
FIG. 1 is a diagram schematically illustrating a configuration of a conventional mammography device.

FIG. 1 is a diagram schematically illustrating a configuration of a conventional mammography device 100. As illustrated in the drawing, the mammography device 100 includes a main body 110, a gantry 120, an X-ray generator 130, a pressing panel 140, and an X-ray detector 150.

The main body 110 is formed of a rectangular housing and is provided with an input device for operating the mammography device 100 and a display device for displaying an image. The main body 110 supports the gantry 120.

The gantry 120 is disposed on one side surface of the main body 110 so as to adjust the height thereof depending on the height of an examinee.

The X-ray generator 130 includes an X-ray source for emitting X-rays and is located at an upper end of the front surface of the gantry 120 so as to vertically irradiate the X-rays toward the X-ray detector 150 on which a patient's breast placed.

The pressing panel 140 is disposed between the X-ray generator 130 and the X-ray detector 150. The pressing panel 140 is movable up and down along a guide groove formed in the vertical direction on the front surface of the gantry 120. The pressing panel 140 provides a function of pressing a patient's breast against the top surface of the X-ray detector 150 disposed at the lower end of the front surface of the gantry 120.

The X-ray detector 150 converts X-rays, which have been generated by the X-ray generator 130 and have passed through a breast, into electrical signals and makes an image.

In such a mammography device 100, the X-ray detector 150 employs a high-contrast image sensor with a pixel size of 70 μm to 100 μm. However, such a high-contrast image sensor is advantageous for detecting an accurate size of a cancer, but has a limit in detecting a very small possible lesion. In general, since a very small possible lesion has a size of 50 μm or less, a high-definition sensor with a pixel size of 50 μm or less is required. However, the X-ray detector 150 in the conventional mammography device 100 employs only a high-contrast image sensor with a pixel size of 70 μm to 100 μm and thus has a problem in that a small possible lesion cannot be detected.

On the other hand, the above-mentioned conventional mammography device 100 can acquire only a two-dimensional (2D) image and thus has a trouble that a breast CT scanning device should be used to acquire a three-dimensional image which can enable ascertaining of an accurate position of a lesion.

In this way, when a breast CT scanning operation is carried out to acquire a three-dimensional image, a particular CT scanning device is used, which is very troublesome. In addition, since a three-dimensional image is captured in a state where a patient lies down and the breast is not pressed, there is a problem in that an accurate image cannot be acquired.

SUMMARY OF THE INVENTION

Technical Problem

Therefore, the present invention is made to solve the above-mentioned problems and an object thereof is to provide a mammography detector having multiple sensors which can improve use convenience of a mammography device by providing a mammography X-ray detector with a high-definition sensor for detecting a very small lesion and a high-contrast sensor for detecting an accurate lesion size.

Another object of the present invention is to provide a mammography detector having multiple sensors which can improve utilization of a mammography device by providing a mammography X-ray detector with a mammography sensor for acquiring a two-dimensional image and a CT sensor for acquiring a three-dimensional image.

Still another object of the present invention is to provide a mammography device which can acquire a three-dimensional image by providing a mammography detector with a mammography sensor and a CT sensor and causing a gantry to rotate by 185 degrees or more in a state where a patient's breast is pressed.

The objects of the present invention are not limited to the above-mentioned objects, but other objects and advantages of the present invention will be understood from the below description and will be understood more apparently from embodiments of the present invention. It will be understood that the objects and advantages of the present invention can be realized by means described in the appended claims and combinations thereof.

Solution to Problem

According to an aspect of the present invention, there is provided a mammography device including: a main body; a gantry that is connected to the main body so as to be vertically movable; an X-ray generator that is attached to one end of the gantry; an X-ray detector that is attached to the other end of the gantry opposing the X-ray generator; first rotating means that is disposed in the main body so as to rotate the gantry; and pressing means for pressing a patient's breast in a state where a patient stands up and including a support panel located on a rotation axis line of the first rotating means and a pressing panel disposed to be vertically movable and to press a breast on the support panel and connected to the main body in a state where the pressing panel is physically separated from the gantry, wherein the X-ray detector includes a CT sensor, and acquires a three-dimensional image while rotating the gantry by a predetermined angle or more in a state where the patient's breast is pressed by the pressing means.

It is preferable that the X-ray detector further includes: a mammography sensor that is disposed on a first surface; the CT sensor that is disposed on a second surface opposed to the first surface; and a readout board that is disposed between the mammography sensor and the CT sensor.

It is also preferable that the X-ray detector further includes an X-ray shielding member that shields the readout board so as to prevent damage and interference of the readout board due to the X-rays generated by the X-ray generator.

It is also preferable that the X-ray detector further includes: a mammography sensor that is disposed on a first surface; the CT sensor that is disposed on a second surface opposed to the first surface; a first readout board that is connected to the mammography sensor so as to communicate with the mammography sensor, to control the mammography sensor, and to read out an image signal; and a second readout board that is connected to the CT sensor so as to communicate with the CT sensor, to control the CT sensor, and to read out an image signal.

It is still preferable that the X-ray detector further includes X-ray shielding members that shield the first and second readout boards so as to prevent damage and interference of the first and second readout board due to the X-rays generated by the X-ray generator.

It is still preferable that the first rotating means causes the gantry to rotate by 185 degrees or more.

Preferably, the mammography device may further include: mode setting means for setting an operation mode of the mammography device; and second rotating means for causing a module of the X-ray detector to automatically rotate on the basis of the mode set by the mode setting means.

Preferably, the X-ray detector further includes display means that is formed on a top surface and/or a bottom surface so as to display a sensor type.

According to another aspect of the present invention, there is provided a mammography detector including: a high-definition sensor that is disposed on a first surface so as to detect a small possible lesion; a high-contrast sensor that is disposed on a second surface opposed to the first surface so as to detect an accurate size of a lesion; and a readout board that is disposed between the high-definition sensor and the high-contrast sensor.

It is preferable that the detector further includes an X-ray shielding member that shields the readout board so as to prevent damage and interference of the readout board due to the X-rays generated by the X-ray generator.

According to still another aspect of the present invention, there is provided a mammography detector including: a high-definition sensor that is disposed on a first surface so as to detect a small possible lesion; a high-contrast sensor that is disposed on a second surface opposed to the first surface so as to detect an accurate size of a lesion; a first readout board that is connected to the high-definition sensor so as to communicate with the high-definition sensor, to control the high-definition sensor, and to read out an image signal; and a second readout board that is connected to the high-contrast sensor so as to communicate with the high-contrast sensor, to control the high-contrast sensor, and to read out an image signal.

It is also preferable that the detector further includes X-ray shielding members that shield the first and second readout boards so as to prevent damage and interference of the first and second readout board due to the X-rays generated by the X-ray generator.

Advantageous Effects

According to the present invention, it is possible to improve use convenience of a mammography device by providing a mammography X-ray detector with a high-definition sensor for detecting a very small lesion and a high-contrast sensor for detecting an accurate lesion size.

According to the present invention, it is possible to acquire a three-dimensional image using the mammography device by providing a mammography X-ray detector with a mammography sensor for acquiring a two-dimensional image and a CT sensor for acquiring a three-dimensional image and causing a gantry to rotate by 185 degrees or more in a state where a patient's breast is pressed.

BEST MODE FOR CARRYING OUT THE INVENTION

The above-mentioned objects, features, and advantages will be described below in detail with reference to the accompanying drawings so as to cause those skilled in the art to easily understand the technical spirit of the present invention. When it is determined in the below description that specific description of known techniques associated with the present invention unnecessarily makes the gist of the present invention vague, detailed description thereof will not be described. Hereinafter, exemplary embodiments of the present invention will be described in detail with reference to the accompanying drawings. In the drawings, like reference numerals are used to represent identical or similar elements.

DESCRIPTION OF EMBODIMENTS

Figure 2:
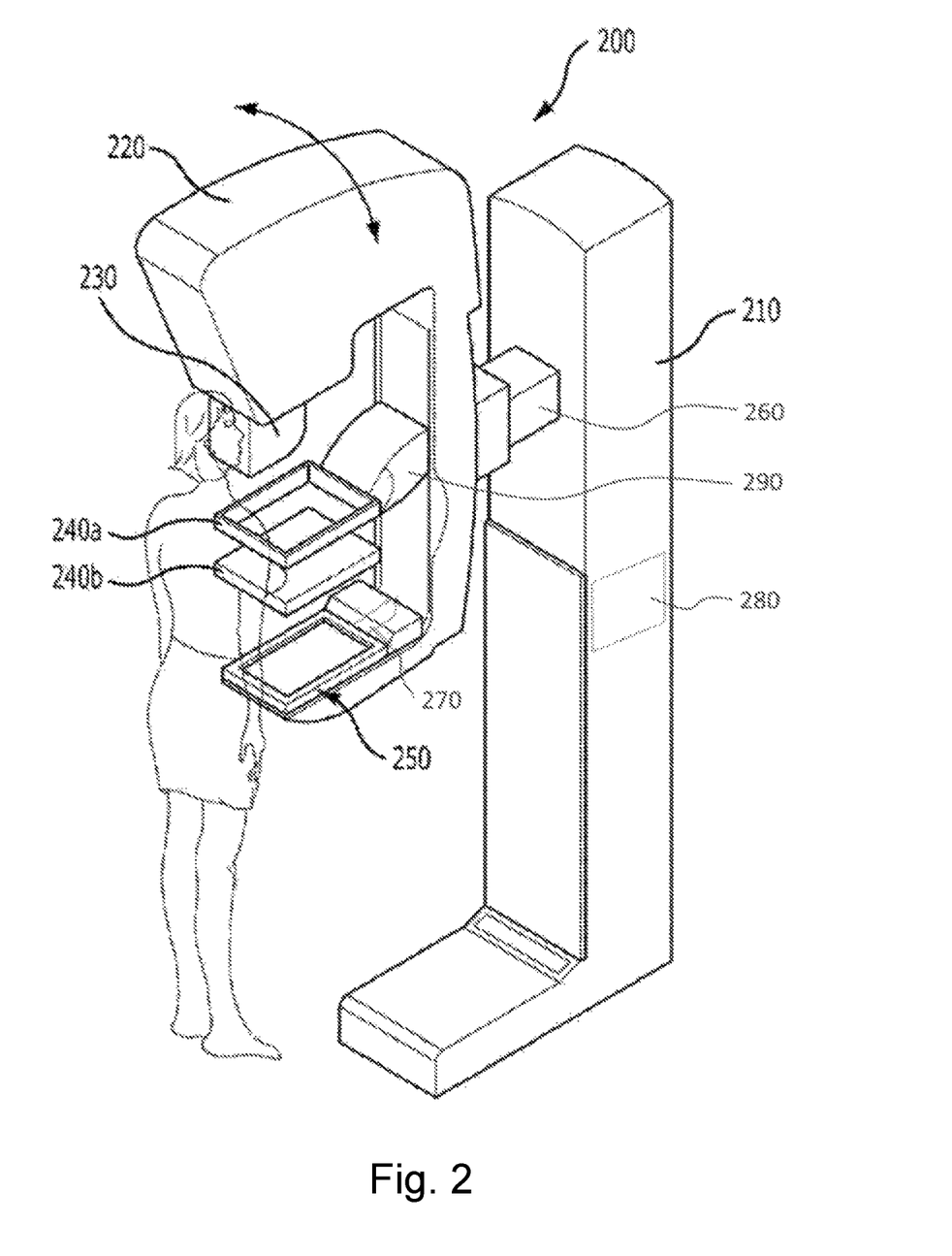
FIG. 2 is a diagram schematically illustrating a configuration of a mammography device capable of acquiring a three-dimensional image according to the present invention.

FIG. 2 is a diagram schematically illustrating a configuration of a mammography device capable of acquiring a three-dimensional image according to the present invention.

As illustrated in FIG. 2, a mammography device 200 according to the present invention includes a main body 210, a gantry 220, an X-ray generator 230, a pressing panel 240a, a support panel 240b, and an X-ray detector 250.

The main body 210 is formed of a rectangular housing and includes an input device, in a predetermined part thereof, for operating the mammography device 200, a display device showing a captured image, and a control module 280 for controlling drive of the gantry 220 and controlling the X-ray detector 250. The main body 210 may have various shapes, and the input device, the display device, and the control module may also be installed at positions separated from the main body 210 as long as they are connected to the main body 210. The main body 210 supports the gantry 220 so as to allow the gantry 220 to rotate.

The gantry 220 is fixed to one side surface of the main body 210, is connected to the main body 210 so as to be rotatable with a rotating shaft 260 attached to be substantially perpendicular to the main body 210, and is connected to the main body 210 so as to be movable in the vertical direction with a sliding member (not illustrated). Accordingly, the gantry 220 can rotate by a predetermined angle with the rotating shaft 260, and the rotating shaft 260 is connected to the sliding member so as to move in the vertical direction relative to the main body 210. Accordingly, the gantry 220 can move along the main body 210 and the height thereof can be appropriately adjusted depending on the position of an examinee.

The X-ray generator 230 includes an X-ray source, provides a function of generating X-rays, and is disposed at an upper end of the front surface of the gantry 220. The lower end of the X-ray generator 230 may be provided with an X-ray shielding film slidably moving in the vertical direction. Accordingly, the height of the X-ray shielding film can be appropriately adjusted depending on a patient's eye height and thus the patient's eyes can be protected from X-rays. The X-ray generator 230 is provided with a collimator or the like and thus provides a function of limiting X-rays so as to emit the X-rays in the vertical direction to irradiate the X-ray detector 250 with the X-rays.

The pressing panel 240a is located between the X-ray generator 230 and the X-ray detector 250, is connected to the main body 210 at a position in the back of the gantry 220 so as to move in the vertical direction, and provides a function of pressing a patient's breast against the support panel 240b located at the lower end of the front surface of the gantry 220 and connected coaxially with the rotating shaft 260.

The support panel 240b is located at the lower end of the front surface of the gantry 220 and serves to support a patient's breast thereon. The pressing panel 240a presses a breast placed on the support panel 240b while moving downward.

Here, the pressing panel 240a and the support panel 240b should be configured to be located coaxially with the rotating shaft 260 after pressing the patient's breast and not to rotate with the rotation of the gantry 220. In other words, the support panel 240b is connected to the rotating shaft 260 so as not to rotate even with the rotation of the gantry 220. The support panel 240b is preferably located substantially coaxially with the rotating shaft 260. The pressing panel 240a may be physically separated from the gantry 220 and is configured not to rotate with the rotation of the gantry 220. That is, the corresponding part of the gantry 220 is provided with a space having a sufficient size so as to cause a connection shaft supporting the pressing panel 240a not to hinder the rotation of the gantry 220 when the gantry 220 rotates in a state where the pressing panel 240a presses the breast. The pressing panel 240a is connected to a support member 290 connected to the main body 210 so as to move in the vertical direction. On the other hand, the pressing panel 240a and the support panel 240b are formed of a material capable of transmitting X-rays.

The X-ray detector 250 provides a function of detecting X-rays generated from the X-ray generator 230 and transmitted through the patient's breast and making an image. The X-ray detector 250 is mounted on a platform connected to the gantry 220 and rotates with the rotation of the gantry 220 at a position corresponding to the X-ray generator 230.

Here, the X-ray detector 250 selectively includes a mammography sensor and a CT sensor formed on a surface opposed to the mammography sensor. The CT sensor is an area type sensor in which unit pixels are two-dimensionally arranged. That is, the CT sensor has a shape in which unit pixels are arranged in a matrix of plural rows and plural columns. The CT sensor rotates about a fixed rotating shaft 270 and receives X-rays emitted from the X-ray generator 230 and transmitted through the patient's breast to acquire an X-ray image of a region of interest of the breast. The CT sensor may be an area sensor having an image acquisition plane with a fixed size capable of acquiring a two-dimensional X-ray image of a region of interest at a time. The X-ray detector 250 may include a high-definition sensor for detecting a very small lesion and a high-contrast sensor for detecting an accurate size of a lesion.

The detailed configuration of the X-ray detector 250 will be described later in more detail with reference to FIGS. 4 to 7.

Figure 3:
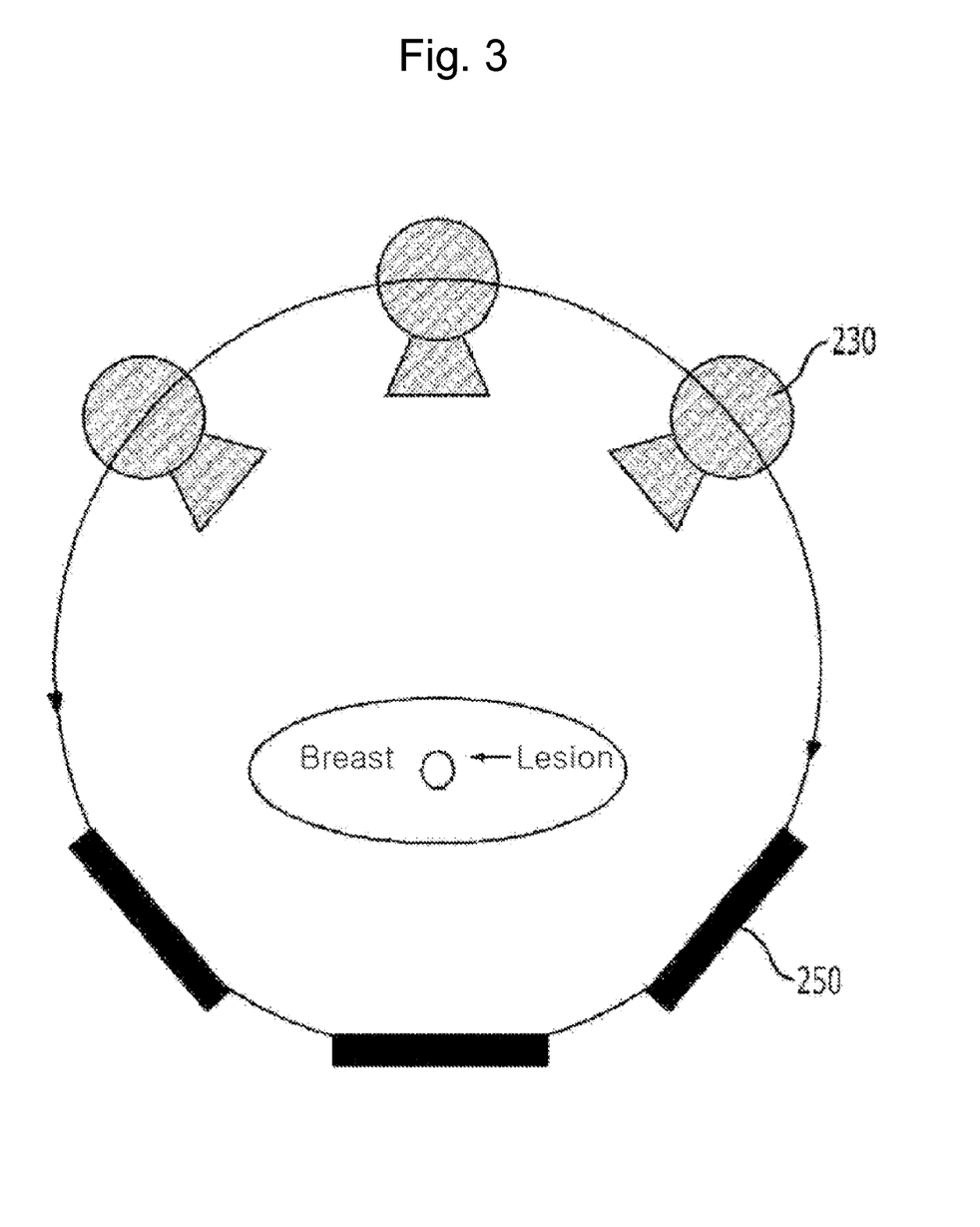
FIG. 3 is a diagram illustrating a three-dimensional image capturing procedure according to the present invention.

FIG. 3 is a diagram illustrating an image capturing operation of a mammography device capable of acquiring a three-dimensional image according to the present invention.

In order to acquire a three-dimensional image, first, the operation mode of the mammography device 200 is set to a CT imaging mode. Accordingly, the CT sensor of the X-ray detector 250 is located in an upper part so as to receive X-rays emitted from the X-ray generator 230. The CT sensor may be located in the upper part using a manual method and an automatic method. The manual method may be carried out by causing an operator of the mammography device 200 to operate the X-ray detector 250 so as to locate the CT sensor in the upper part. The automatic method may be carried out by causing the X-ray detector 250 to automatically rotate so as to locate the CT sensor in the upper part depending on the set mode using a sensing circuit for sensing a position of the CT sensor and a drive circuit for rotationally driving the X-ray detector 250. The technique of automatically setting the X-ray detector 250 can be easily implemented by those skilled in the art using known techniques and specific description thereof will not be made in the following description.

After the X-ray detector 250 is operated so as to locate the CT sensor thereof in the upper part in this way, the gantry 220 moves vertically to locate the patient's breast on the support panel 240b. In this state, the pressing panel 240a moves to press the breast placed on the support panel 240b. Then, the breast is irradiated with X-rays from the X-ray generator 230 while rotating the gantry 220 by 185 degrees or more. Accordingly, the X-ray generator 230 and the X-ray detector 250 rotate at the corresponding positions and the X-ray detector 250 acquires an image of the breast in the directions of 185 degrees or more.

A three-dimensional image can be acquired using the two-dimensional image acquired in this way with rotation of 185 degrees or more. In the present invention, the gantry 220 may rotate by 360 degrees. However, a three-dimensional images can be constructed using even the two-dimensional images acquired with the rotation of 185 degrees or more.

Figure 4:
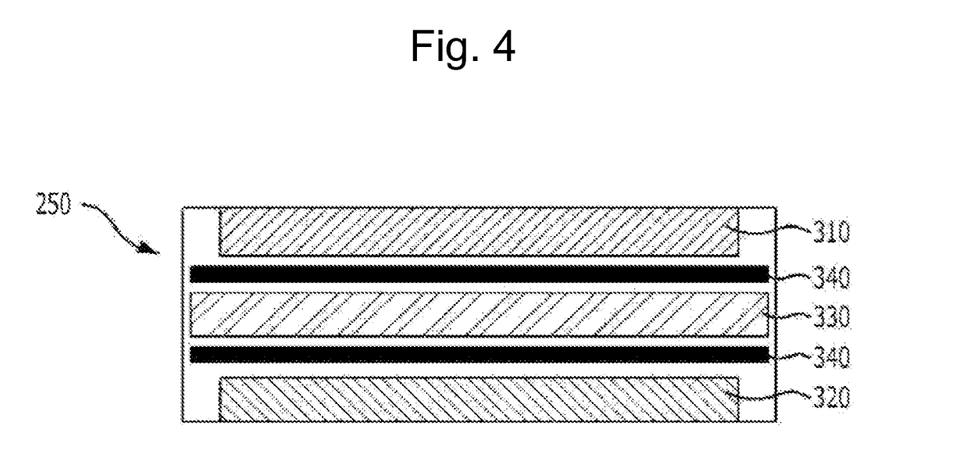
FIG. 4 is a diagram schematically illustrating a configuration of a mammography detector having multiple sensors according to an embodiment of the present invention.

FIG. 4 is a cross-sectional view schematically illustrating a configuration of a mammography x-ray detector 250 having multiple sensors according to an embodiment of the present invention.

The multiple sensors may include a high-definition sensor for detecting a very small lesion and a high-contrast sensor for detecting an accurate size of a lesion. The multiple sensors may include a general mammography sensor for acquiring a two-dimensional image and a CT sensor for acquiring a three-dimensional image. Here, the sensors are referred to as a first sensor and a second sensor, respectively.

Referring to FIG. 4, the mammography X-ray detector 250 roughly includes a first sensor 310 disposed on a first surface, a second sensor 320 disposed on a second surface opposed to the first surface, and a readout board 330 disposed between the first sensor 310 and the second sensor 320 so as to read electrical signals formed by the first and second sensors 310 and 320 or to control the first and second sensors 310 and 320.

The first sensor 310 may be high-contrast sensor or a mammography sensor and is disposed on the first surface of the X-ray detector 250. The second sensor 320 may be a high-definition sensor or a CT sensor and is disposed on the second surface opposed to the first surface. Here, if adopting an indirect type, the first and second sensors 310 and 320 include a semiconductor image sensor array and a fluorescent panel and have modulated forms. Therefore, the X-ray detector 250 includes a housing, the first sensor 310 is fixed and combined to the first surface of the housing, and the second sensor 320 is fixed and combined to the second surface of the housing.

The readout board 330 is disposed in the housing of the X-ray detector 250 between the first sensor 310 and the second sensor 320. The readout board 330 is coupled to the first and second sensors 310 and 320 so as to communicate therewith and performs a function of controlling the first and second sensors 310 and 320 and reading and transmitting image signals generated by the first and second sensors 310 and 320 to a computer for processing an image.

On the other hand, in order to prevent the X-rays emitted from the X-ray generator 230 from damaging the readout board 330 or interfering with circuits in the readout board 330, the readout board 330 is shielded with an X-ray shielding member 340.

In an embodiment of the present invention, the first and second sensors 310 and 320 share a single readout board 330.

Figure 5:
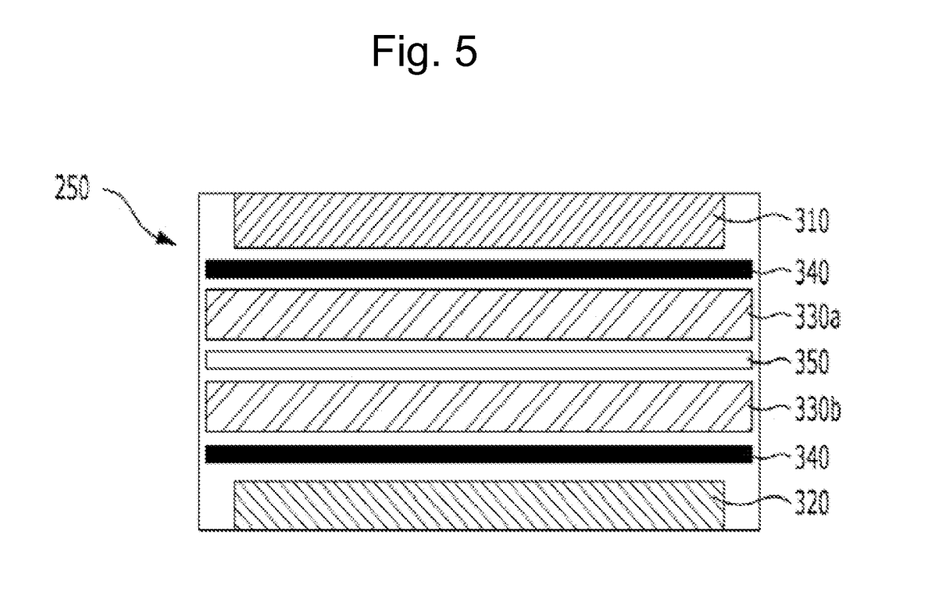
FIG. 5 is a diagram schematically illustrating a configuration of a mammography detector having multiple sensors according to another embodiment of the present invention.

FIG. 5 is a cross-sectional view schematically illustrating a configuration of a mammography X-ray detector 250 having multiple sensors according to another embodiment of the present invention.

In another example of the mammography X-ray detector according to the present invention illustrated in FIG. 5, the first and second sensors 310 and 320 have readout boards 330a and 330b, respectively, unlike FIG. 4.

Referring to FIG. 5, the mammography X-ray detector 250 roughly includes a first sensor 310 disposed on a first surface, a second sensor 320 disposed on a second surface opposed to the first surface, and a first readout board 330a configured to control the first sensor 310 and to read an image signal formed by the first sensor 310, and a second readout board 330b configured to control the second sensor 320 and to read an image signal formed by the second sensor 320.

The first sensor 310 may be a high-contrast sensor or a mammography sensor and is disposed on the first surface of the X-ray detector 250. The second sensor 320 may be a high-definition sensor or a CT sensor and is disposed on the second surface opposed to the first surface. Here, if adopting an indirect type, the first and second sensors 310 and 320 include a semiconductor image sensor array and a fluorescent panel and have modulated forms. Therefore, the X-ray detector includes a housing, the first sensor 310 is fixed and combined to the first surface of the housing, and the second sensor 320 is fixed and combined to the second surface of the housing.

The first readout board 330a and the second readout board 330b are disposed in the housing of the X-ray detector 250 between the first sensor 310 and the second sensor 320. The first readout board 330a is coupled to the first sensor 310 so as to communicate therewith and performs a function of controlling the first sensor 310 and reading and transmitting an image signal generated by the first sensor 310 to a computer for processing an image. The second readout board 330b is coupled to the second sensor 320 so as to communicate therewith and performs a function of controlling the second sensor 320 and reading and transmitting an image signal generated by the second sensor 320 to a computer for processing an image.

In order to prevent the X-rays emitted from the X-ray generator 230 from damaging the first and second readout boards 330a and 330b or interfering with circuits in the readout boards 330a and 330b, the first and second readout boards 330a and 330b are shielded with X-ray shielding members 340, respectively. On the other hand, an insulating member 350 for electrically insulating the first and second readout boards 330a and 330b from each other may be disposed between the first and second readout boards 330a and 330b.

Figure 6:
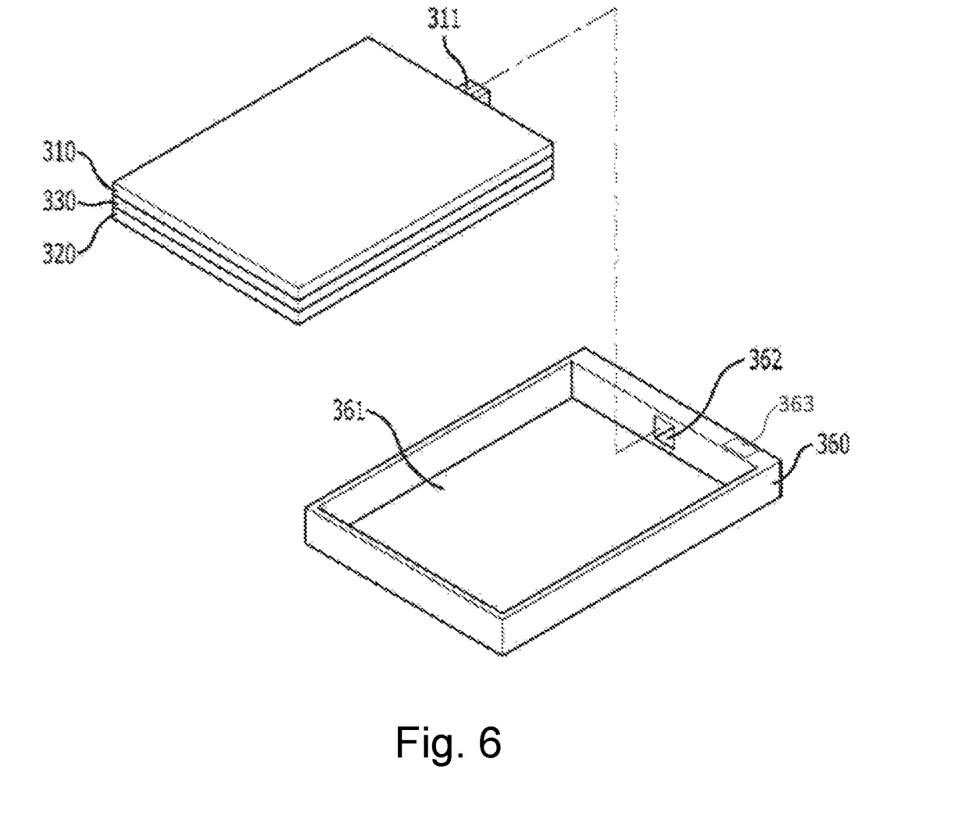
FIG. 6 is a diagram illustrating a detailed appearance of the mammography detector having multiple sensors according to the present invention.

FIG. 6 is a diagram illustrating a detailed appearance of the mammography detector 250 having multiple sensors according to the present invention.

Referring to FIG. 6, the mammography detector 250 includes a support frame 360 that is fixed and coupled to the gantry 220 and that supports the mammography detector 250. The support frame 360 is provided with a reception part 361 for receiving the mammography detector 250 and is provided with a connector insertion hole 362 into which a connector 311 for communicable connection with the readout board of the mammography detector 250.

One end of the mammography detector 250 is provided with the connector 311 connected to a communication cable built in the gantry 220. A display device 363 for displaying a sensor type or a switch capable of automatically recognizing a sensor type may be formed on the first surface and the second surface of the mammography detector 250.

The present invention can be replaced, modified, and changed in various forms without departing from the technical thought of the present invention by those skilled in the art and is not limited to the above-mentioned embodiments or the accompanying drawings.

INDUSTRIAL APPLICABILITY

According to the present invention, it is possible to improve use convenience of a mammography device by providing a mammography X-ray detector with a high-definition sensor for detecting a very small lesion and a high-contrast sensor for detecting an accurate lesion size.

The invention claimed is:
1. A mammography device comprising:
   a main body;
   a gantry connected to the main body to be vertically movable;
   an X-ray generator attached to one end of the gantry;
   an X-ray detector attached to the other end of the gantry opposing the X-ray generator;
   a first rotating shaft disposed in the main body and configured to rotate the gantry;

a support panel disposed on a rotation axis line of the first rotating shaft and configured to support a patient's breast; and a pressing panel configured to press the patient's breast on the support panel, where the pressing panel is vertically movably disposed, and connected to the main body, wherein the X-ray detector includes a first sensor disposed on a first surface and a second sensor disposed on a second surface opposed to the first surface and acquires a three-dimensional image while rotating the gantry by a predetermined angle or more in a state where the patient's breast is pressed by the pressing panel and the support panel.

2. The mammography device according to claim 1, further comprising a readout board disposed between the first sensor and the second sensor.

3. The mammography device according to claim 2, wherein the X-ray detector further includes an X-ray shielding member that shields the readout board so as to prevent damage and interference of the readout board due to X-rays generated by the X-ray generator.

4. The mammography device according to claim 1, wherein the first sensor is a high-definition sensor that is disposed on the first surface of the X-ray detector, and the second sensor is a high-contrast sensor that is disposed on the second surface of the X-ray detector so as to be opposed to the first surface, and wherein the mammography device further comprises a readout board that is disposed between the high-definition sensor and the high-contrast sensor.

5. The mammography device according to claim 4, wherein the X-ray detector further includes X-ray shielding members that shield a readout board so as to prevent damage and interference of the readout board due to X-rays generated by the X-ray generator.

6. The mammography device according to claim 1, wherein the first rotating shaft causes the gantry to rotate by about 185 degrees or more.

7. The mammography device according to claim 1, further comprising:
a control module configured to set an operation mode of the mammography device; and a second rotating shaft configured to cause a module of the X-ray detector to automatically rotate on the basis of the mode set by the mode setting means.

8. The mammography device according to claim 7, wherein the X-ray detector further includes a display device that is formed on a top surface and/or a bottom surface so as to display a sensor type.

9. The mammography device according to claim 1, wherein the first sensor is a high-definition sensor that is disposed on the first surface so as to detect a small possible lesion, and the second sensor is a high-contrast sensor that is disposed on the second surface opposed to the first surface so as to detect an accurate size of a lesion, and wherein the mammography device further comprises a readout board that is disposed between the high-definition sensor and the high-contrast sensor.

10. The mammography device according to claim 9, wherein the detector further includes an X-ray shielding member that shields the readout board so as to prevent damage and interference of the readout board due to X-rays generated by the X-ray generator.

11. The mammography device according to claim 9, wherein the high-definition sensor has a pixel size of about 50 μm or less and the high-contrast sensor has a pixel size of about 70 μm to about 100 μm.

12. The mammography device according to claim 1, wherein the x-ray detector further includes a readout board, the readout board includes:
a first readout board that is connected to the first sensor so as to communicate with the first sensor, to control the first sensor, and to read out an image signal; and
a second readout board that is connected to the second sensor so as to communicate with the second sensor, to control the second sensor, and to read out an image signal.

13. The mammography device according to claim 12, wherein mammography devices further comprises X-ray shielding members that shield the first readout board and second readout board so as to prevent damage and interference of the first readout board and second readout board due to the X-rays generated by the X-ray generator.

* * * * *